(12) United States Patent
Tang et al.

(10) Patent No.: US 11,139,049 B2
(45) Date of Patent: Oct. 5, 2021

(54) SUPPRESSING INTERACTION BETWEEN BONDED PARTICLES

(71) Applicant: D.E. SHAW RESEARCH, LLC, New York, NY (US)

(72) Inventors: Ping Tak Peter Tang, Edison, NJ (US); J. P. Grossman, Huntington, NY (US); Brannon Batson, Brooklyn, NY (US); Ron Dror, Standford, CA (US)

(73) Assignee: D.E. Shaw Research, LLC, New York, NY (US)

( * ) Notice: Subject to any disclaimer, the term of this patent is extended or adjusted under 35 U.S.C. 154(b) by 681 days.

(21) Appl. No.: 15/526,846

(22) PCT Filed: Nov. 16, 2015

(86) PCT No.: PCT/US2015/060863
§ 371 (c)(1),
(2) Date: May 15, 2017

(87) PCT Pub. No.: WO2016/077823
PCT Pub. Date: May 19, 2016

(65) Prior Publication Data
US 2019/0087546 A1    Mar. 21, 2019

Related U.S. Application Data

(60) Provisional application No. 62/079,681, filed on Nov. 14, 2014.

(51) Int. Cl.
*G16C 10/00* (2019.01)
*G16C 20/90* (2019.01)

(52) U.S. Cl.
CPC .............. *G16C 10/00* (2019.02); *G16C 20/90* (2019.02)

(58) Field of Classification Search
CPC ....................................................... G16C 10/00
(Continued)

(56) References Cited

U.S. PATENT DOCUMENTS

| 5,241,470 A | * | 8/1993 | Lee | G16B 15/20 |
| | | | | 436/86 |
| 5,553,004 A | * | 9/1996 | Gronbech-Jensen | G16B 15/00 |
| | | | | 702/19 |

(Continued)

OTHER PUBLICATIONS

Treacy et al. ("Schla ⁻¦ cluster topological analysis of medium range order in paracrystalline amorphous semiconductor models", Journal of Non-Crystalline Solids, 2000, pp. 150-155) (Year: 2000).*

(Continued)

*Primary Examiner* — Iftekhar A Khan
(74) *Attorney, Agent, or Firm* — Occhiuti & Rohlicek LLP

(57) ABSTRACT

A method comprising causing a simulation machine for molecular dynamic simulation to determine that a topological distance that separates two particles is less than a threshold. The simulation machine includes nodes connected by a network. The nodes collectively representing a volume with each node corresponding to a portion of the simulation space. A topological relationship between the nodes corresponds to spatial relationship thereof in the simulation space. The simulation volume is occupied by particles that interact with each other. The two particles are among these particles. The simulation volume includes node boxes, each of which is handled by one of the nodes. Each of the nodes is implemented as an application specific integrated circuit that includes a combination of first and second hardware elements. The first hardware elements are especially designed to perform pairwise interactions. The second hardware elements operate to provide potentially interacting particles to the first hardware elements.

29 Claims, 5 Drawing Sheets

FIG. 1A

(58) Field of Classification Search
USPC ............................................................ 703/2
See application file for complete search history.

(56) References Cited

U.S. PATENT DOCUMENTS

| | | | | |
|---|---|---|---|---|
| 5,915,230 | A * | 6/1999 | Berne | C07K 1/113 702/22 |
| 6,373,489 | B1 * | 4/2002 | Lu | G06T 17/20 345/428 |
| 6,407,748 | B1 * | 6/2002 | Xavier | G06T 19/20 345/419 |
| 6,678,642 | B1 * | 1/2004 | Budge | G06F 30/23 703/2 |
| 7,096,167 | B2 * | 8/2006 | Zhou | G16B 15/00 703/2 |
| 8,126,956 | B2 * | 2/2012 | Bowers | G06F 15/76 709/201 |
| 8,571,806 | B2 * | 10/2013 | Desmet | C07K 1/00 702/19 |
| 2004/0087503 | A1 * | 5/2004 | Carr | A61K 38/185 424/185.1 |
| 2005/0037969 | A1 * | 2/2005 | Lu | C07K 14/4702 424/133.1 |
| 2007/0276791 | A1 * | 11/2007 | Fejes | G06F 17/13 |
| 2008/0201121 | A1 * | 8/2008 | Yano | G16C 10/00 703/2 |
| 2008/0243452 | A1 * | 10/2008 | Bowers | G06F 30/25 703/2 |
| 2010/0329930 | A1 * | 12/2010 | Salemme | G01N 33/53 422/69 |
| 2011/0125478 | A1 * | 5/2011 | Guest | G16C 20/30 703/12 |
| 2011/0248157 | A1 * | 10/2011 | Sugiyama | H01J 49/063 250/282 |
| 2011/0262963 | A1 * | 10/2011 | Geierstanger | C07K 5/0215 435/68.1 |
| 2011/0313741 | A1 * | 12/2011 | Langhoff | G16C 20/30 703/2 |
| 2012/0171693 | A1 * | 7/2012 | Arnold | G16B 30/10 435/6.18 |
| 2014/0257769 | A1 * | 9/2014 | Sakharnykh | G16C 10/00 703/2 |
| 2014/0282576 | A1 * | 9/2014 | Grossman | G06F 9/4881 718/103 |
| 2015/0051090 | A1 * | 2/2015 | Shan | G16B 15/00 506/8 |
| 2016/0350474 | A1 * | 12/2016 | Zheng | G16C 20/50 |
| 2017/0323049 | A1 * | 11/2017 | Cheremovsky | G16C 20/50 |
| 2017/0329892 | A1 * | 11/2017 | Fan | G16B 40/20 |
| 2018/0042843 | A1 * | 2/2018 | Blum | C07K 14/001 |

OTHER PUBLICATIONS

Hallen et al. ("Dead-End Elimination with Perturbations ("DEEPer"): A provable protein design algorithm with continuous sidechain and backbone flexibility", NIH publications, pp. 1-43) (Year: 2013).*
Shaw et al. ("Anton, a Special-Purpose Machine for Molecular Dynamics Simulation", ISCA, 2007, pp. 1-12) (Year: 2007).*

* cited by examiner

SUPPRESSING INTERACTION BETWEEN BONDED PARTICLES

CROSS-REFERENCE TO RELATED APPLICATIONS

This application is the national stage entry under 35 USC 371 of PCT/US2015/060863, filed on Nov. 16, 2015, which claims the benefit of the Nov. 14, 2014 priority date of U.S. application 62/079,681, the contents of which are herein incorporated by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all rights whatsoever.

FIELD OF DISCLOSURE

This disclosure relates to simulation of molecular dynamics, and in particular, to avoiding unnecessary computations of interactions between particle pairs and managing flow of data representative of particles into and out of queues.

BACKGROUND

A molecular dynamics simulation machine attempts to simulate the evolution of a system that is made of particles that interact with each other. The interaction between particles arises from forces acting at a distance. An example of such a force is the gravitational force. Another example is the electrical force.

Simulation of particle dynamics typically involves summing all forces that act on a particle and then using Newton's laws to determine the motion of the particle as a result of the summation of those forces. In principle, each particle experiences forces from all other particles in the system. However, the magnitudes of these forces typically fall off with the square of the distance between particles. Therefore, as a practical matter, it is preferable to carry out computations only when particles are close enough to make a difference.

Details of the structure and function of a known simulation machine 10 can be found in U.S. Pat. No. 8,126,956 and in WO2006/113825, the contents of which are herein incorporated by reference.

SUMMARY

The invention concerns improvements to the apparatus and methods described in Bowers, et al., "DETERMINING COMPUTATION UNITS FOR COMPUTING MULTIPLE BODY INTERACTIONS," U.S. Pat. No. 8,126,956, issued Feb. 28, 2012. These improvements include suppression of unnecessary computation between particles and improved management of the flow of simulated particles into queues.

The invention is based in part on the recognition that there are other reasons to suppress computation of interaction between particles besides distance. Thus, even when particles are very close to each other, there may be reasons to suppress computation of interaction between those particles. The invention thus provides a way to identify such particle pairs and to suppress computation of interaction between such particle pairs, thereby improving computational performance of a molecular dynamics simulator.

In a first aspect, the invention features a method that includes causing a computer to determine that a topological distance between two particles is less than a threshold.

Some practices include, based on the determination, causing the computer to suppress computation of an interaction between the two particles.

Other practices include providing a computer-readable graph representing a relationship between the particles, wherein the topological distance depends at least in part on a number of edges between the two particles in the graph. Among these are embodiments in which the particles include first and second atoms. In some of these practices, suppressing computation of an interaction between the two particles comprises suppressing computation that, if unsuppressed, would be carried out by a molecular dynamics simulation system.

Other practices include those in which determining that a topological distance between the two particles is less than a threshold includes tagging a first of the particles with a first topological identifier indicative of a topological relationship between the first particle and a set of particles of which it is a part. Among these are embodiments in which the first particle is an atom and the set of particles is a molecule formed by covalently bonds between pairs of particles.

Additional practices include tagging a second of the particles with a second topological identifier, and determining a topological distance between the first and second particles based on the first and second topological identifiers. Among these practices are those in which each of the first and second topological identifiers comprises a backbone identifier, those in which each of the topological identifiers comprises at least one side-chain identifier, those in which each of the topological identifiers comprises a termination flag, and those in which each of the first and second topological identifiers comprises a backbone identifier, a primary side-chain identifier, a secondary side-chain identifier, and a termination flag.

A variety of ways to calculate topological distance are within the scope of the claims. For example, one practice includes doing so by adding together a magnitude of a difference between backbone identifiers of the first and second topological identifiers, primary side-chain identifiers of the first and second topological identifiers, secondary side-chain identifiers of the first and second topological identifiers, and terminal identifiers of the first and second topological identifiers. Another practice includes doing so by adding together a magnitude of a difference between primary side-chain identifiers of the first and second topological identifiers, secondary side-chain identifiers of the first and second topological identifiers, and terminal identifiers of the first and second topological identifiers. Yet another practice includes doing so by adding together a magnitude of a difference between secondary side-chain identifiers of the first and second topological identifiers, and terminal identifiers of the first and second topological identifiers.

Some practices include the additional step of determining that the graph has a cyclic portion, and modifying the graph to eliminate the cyclic portion prior to assigning topological identifiers to particles represented in the graph.

In another aspect, the invention features a non-transitory and tangible computer-readable medium having encoded thereon software that, when executed by a computer system, causes execution of any of the foregoing methods.

In another aspect, the invention features an apparatus comprising a computer system configured to execute any of the foregoing methods.

In another aspect, the invention features a method that includes determining that a topological distance between two particles is less than a threshold.

In yet another aspect, the invention features a molecular dynamics simulator configured to execute any of the foregoing methods.

In a second aspect, the invention features a method for managing flow of particles into an array of pairwise-point-interaction-modules. Such a method includes receiving a first set of particles into a first queue, the first set of particles being a proper subset of a second set of particles that comprises all particles that are to be passed into an array of pairwise-point-interaction-modules during a current time period, and prior to having received all particles from the second set, allowing the particles from the first set to pass from the first queue into the array.

In one practice, the method includes continuing to load particles from the first set into the array as additional particles from the second set are received into the first queue.

In another practice, the method includes receiving a third set of particles into a second queue. This third set of particles comprises all particles that are to only be loaded into the array during the current time period. In such a practice, allowing the particles from the first set to pass from the first queue into the array occurs only after all particles from the third set have been loaded into the array.

In yet another practice, the method includes receiving a third set of particles into second and third queues. The third set of particles comprises all particles that are to be loaded into the array during the current time period. In this practice, allowing the particles from the first set to pass from the first queue into the array occurs only after all particles from the third set have been loaded into the array.

In further practices, the method includes receiving a fourth set of particles into a third queue. The fourth set of particles is to be both loaded and streamed into the array. In this practice, streaming of particles from the fourth set commences only after completion of loading of particles from the fourth set.

Additional practices include those in which the first queue is a logical queue. These practices include selecting the first and second set of particles from a plurality of selected physical queues.

In another aspect, the invention includes a non-transitory and tangible computer-readable medium having encoded thereon software that, when executed by a computer system, causes execution of the methods associated with the second aspect of the invention.

In another aspect, the invention includes an apparatus comprising a computer system configured to execute any one of the methods associated with the second aspect of the invention.

In another aspect, the invention includes a molecular dynamics simulator configured to execute any one of the of the methods associated with the second aspect of the invention.

These and other aspects of the invention will be apparent from the following detailed description and the accompanying figures, in which:

DETAILED DESCRIPTION

Molecular dynamics simulation involves simulating the motion of particles in response to forces. Because many of these forces are short-range forces, most computations involving a particle are restricted to interactions with nearby particles. Thus, computations involving a neighborhood of particles can often be carried out largely independently of computations involving other neighborhoods of particles. This property lends itself to parallel processing.

Figure 1:
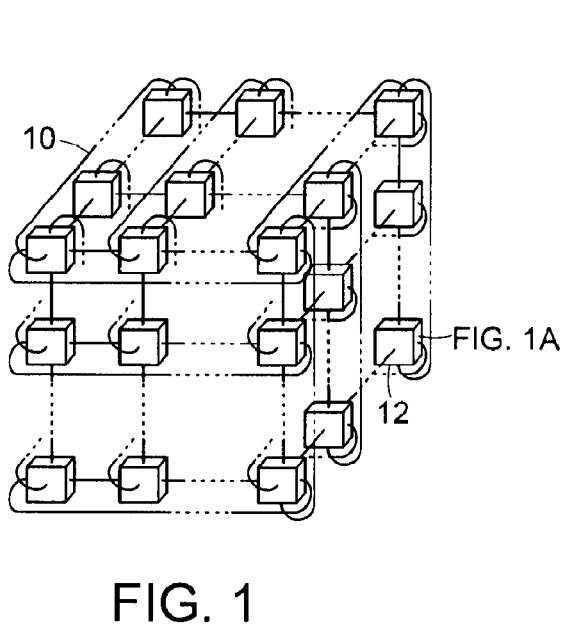
FIG. 1 shows some of the nodes in an exemplary molecular dynamics simulation machine, and the architecture of a typical node.
Figure 1A:
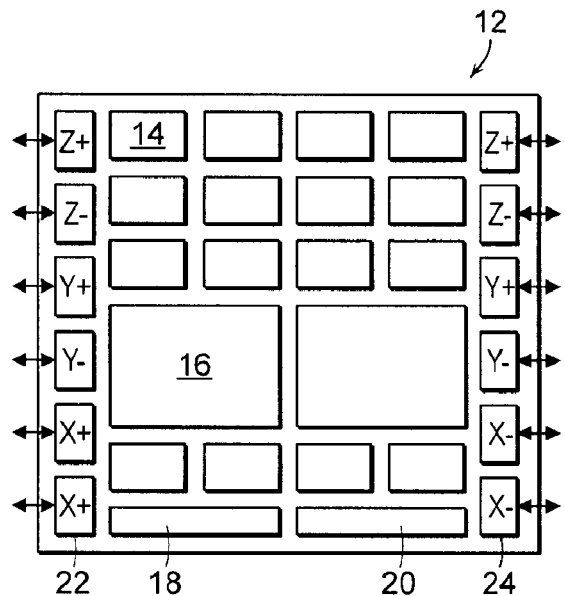

To take advantage of this inherent parallelism, a simulation machine 10 for molecular dynamic simulation, as shown in FIG. 1, features a plurality of nodes 12 that are connected by a network. The nodes collectively represent a volume of a simulation space, with each node corresponding to a particular portion of that simulation space. The topological relationship between nodes in the network corresponds to their spatial relationship in the simulation space. This simulation volume is occupied by particles that interact with each other in ways that are to be calculated by the simulation machine 10. In one particular embodiment, the simulation volume is toroidal. However, other volumes are possible, such as prisms.

Because of the inherent parallelism, it is useful to divide the simulation volume into node boxes, each of which is handled by one of the nodes 12. A description of the manner in which calculations are allocated among different nodes can be found in Shaw, "ORTHOGONAL METHOD," U.S. Pat. No. 7,707,016, issued Apr. 7, 2010, the contents of which are herein incorporated by reference.

Each node 12 is implemented as a combination of first hardware elements that are especially designed to perform pairwise interactions and second hardware elements whose function is to provide potentially interacting particles to the first hardware elements. In one embodiment, each node 12 is implemented as an application specific integrated circuit having sixteen flex tiles 14, two interaction tiles 16, a host interface 18, and a logic analyzer 20.

The host interface 18 provides communication with an external host via a PCI link. The logic analyzer 20 is used primarily to capture and store node activity for debugging. Each node 12 also includes communication interfaces 22 for data transmission between neighboring nodes in each of the three local coordinate directions. Within a node 12, data transmission between the components of the node 12 is carried out by an on-chip mesh network.

Figure 2:
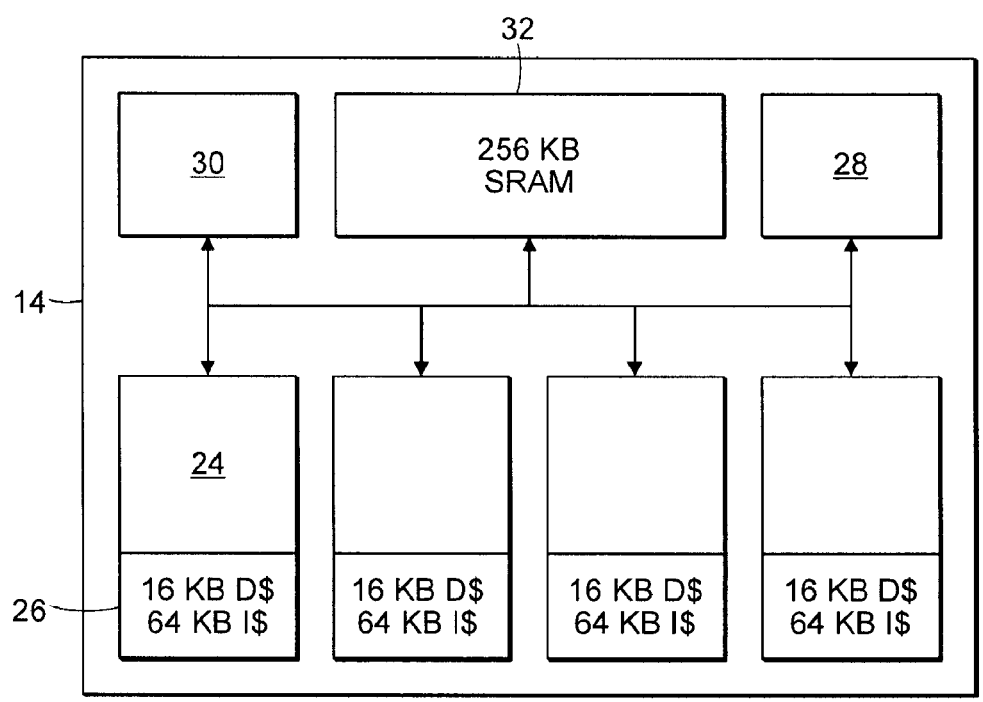
FIG. 2 shows the architecture of a flex tile from FIG. 2.

As shown in FIG. 2, each flex tile 14 has geometry cores 24, each of which has an associated memory 26. In the particular embodiment shown, there are four such geometry cores 24. However, in general other numbers of geometry cores can be used. Each flex tile 14 also includes a network interface 28 for enabling communication with other components of the node 12, and a dispatch unit 30 to provide hardware support for fine-grained event-driven computation. A dispatch unit 30 is described in detail in Grossman, "EVENT-DRIVEN COMPUTATION," U.S. Patent Publ. 2014-0282576, filed on Sep. 18, 2014, the contents of which are herein incorporated by reference. Also included in a flex tile is a common memory 32 that is available to all four geometry cores 24.

Figure 3:
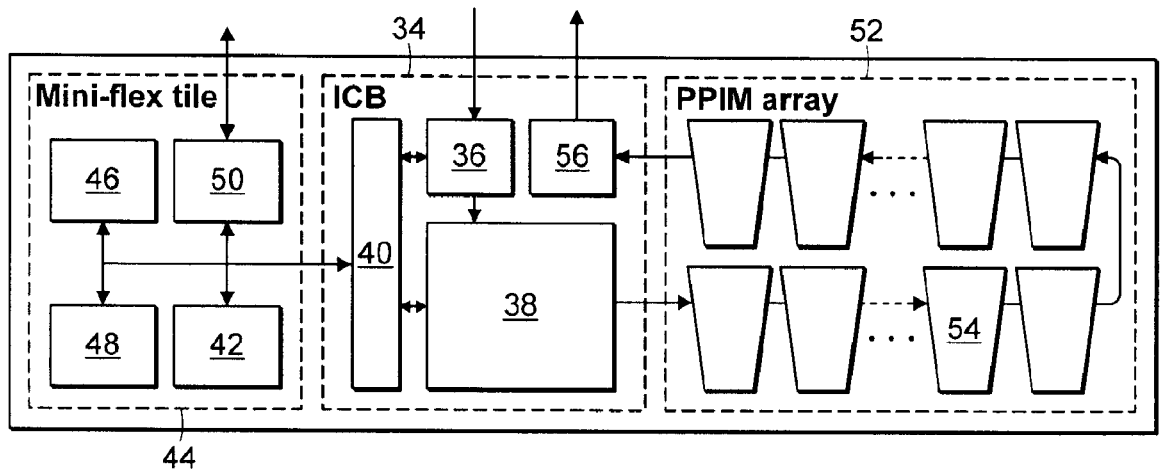
FIG. 3 shows the architecture of an interaction tile from FIG. 1.

As shown in FIG. 3, each interaction tile 16 features an interaction controller 34, an abbreviated flex tile 44, and a pairwise-point-interaction-module ("PPIM") array 52. PPIM array 52 is made up of PPIMS 54. Pairwise interaction between particles occurs in the PPIM array 52. In the illustrated embodiment, the PPIM array 52 has thirty-eight PPIMS 54. However, in general, other numbers of PPIMS can be used.

The interaction tile 16, and specifically the interaction controller 34, receives particles and grid points from the flex tiles 14 via the on-chip mesh network. It then enqueues these particles and grid points into queues 36 that are stored in local memory 38. The operation of the interaction controller 34 is controlled by instructions 40 received from a geometry core 42 in the abbreviated flex tile 44.

In addition to a geometry core 42, the abbreviated flex tile 44 has a local memory 46, a dispatch unit 48, and a network interface 50, all of which serve functions similar to those described in connection with FIG. 2.

The simulation machine 10 simulates the evolution of a collection of particles by repeatedly calculating and integrating all inter-particle forces in small time steps. At the beginning of each time step, each flex tile 14 uses the on-chip network to send packets to interaction tiles 16 on the same node and on other nodes. These packets contain information about particles that interact with each other in ways that the interaction tile 16 will ultimately reveal through calculation.

As noted above, each node 12 is responsible for computations concerning particles within its node box. Due to resource limitations, it may be necessary to further divide each node box into sub-boxes. Each sub-box has some particle population. This particle population fluctuates over time as a result of particles moving within the simulation volume in response to forces exerted by other particles. Each interaction tile 16 will receive, from the flex tiles 14, some variable number of particles from multiple sub-boxes. Each interaction tile 16 also receives, from the flex tiles 14, count packets, each of which reports how many particles to expect from each sub-box. These count packets are used by the interaction tile 16 to determine when it has received all particles from all sub-boxes.

To accurately simulate the motion of particles, it has been found necessary to evaluate particle interactions at time intervals that are very close together. In a typical simulation, particle interactions are evaluated every few femtoseconds of simulated time.

Many interesting events occur on timescales of milliseconds or longer, involve hundreds of thousands of particles, or both. Examples of events of this type include those that arise in biochemical systems in which biological macromolecules interact.

Simulation of systems in which events unfold on such long time scales takes a great deal of real time. This is because the exchange rate between simulation time and real time is presently on the order of a billion to one. Thus, it is necessary to spend microseconds in order to compute the interactions required to advance the simulated time by femtoseconds. While this may seem fast, to place matters in perspective, this means that in order to simulate just one millisecond of real time at this exchange rate, it is necessary for the simulation machine 10 to work for one million seconds, which is a little over eleven days of continuous computation.

The following discussion refers to particles being stored in or streaming through certain hardware. It should be understood that a "particle" means information representing a particle, or a simulated particle, and not actual particles.

Figure 7:
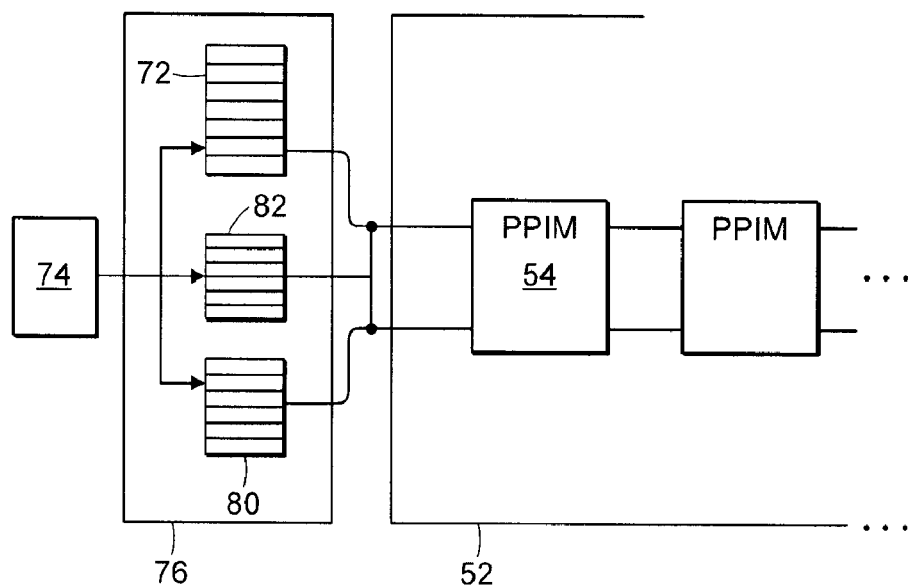
FIG. 7 shows queues in the high-throughput interaction-subsystem tile of FIG. 3.

Particles arrive at an interaction tile 16 in no particular order. As they arrive, a particle director 74 places them into different first-in-first-out (FIFO) queues 76, as shown in FIG. 7. In one embodiment, there are $2^7$ such queues 76. In one implementation, the particle director 74 is implemented as a programmable look-up table.

Since particles arrive in no particular order, they are also placed in queues 76 in no particular order. However, the order in which queues 76 will be used is known in advance. Additionally, each queue is programmed in advance to know how many sub-boxes worth of particles it is expecting. Because of the count packets being received from the flex tiles 14, each queue can also determine how many particles will arrive for each sub-box. As a result, each queue 76 knows how many particles to expect, and whether or not they have all arrived.

The queues 76 are divided into first queues 78, second queues 80, and third queues 82. Particles that are to be loaded into the PPIM array 52 are placed in a first queue 78. Particles that are to be streamed past the loaded particles are placed in a second queue 80. Particles that are to be both loaded and streamed are placed in a third queue 82.

For example, particles that are only within a first volume of space are placed in the first queue 78, from which they are loaded into the PPIM array 52. Particles that are in only a second volume of space are placed in the second queue 80, from which they are streamed into the PPIM array 52. And, particles that are in the intersection of the first and second volumes of space are placed in the third queue 82, from which they are both loaded and streamed into the PPIM array 52.

In one embodiment, the interaction controller 34 waits until the first and third queues 78, 82 have been filled. As noted above, this information is available because the flex tiles 14 have been sending count packets along with the particles. The interaction controller 34 then loads all the particles from the first and third queues 78, 82 into the PPIMS 54 in a round-robin fashion. Once the particles have been loaded, the PPIM array 52 is ready to accept the streaming particles from the second queue 80 and again from the third queue 82. Control over whether a queue is to begin allowing its particles into the PPIM array 52 or whether it should wait is carried out by software instructions.

Upon detecting that loading is complete, the interaction controller 34 determines whether the second queue 80 is full. The third queue 82 is of course known to be full by this point since loading into the PPIM array 52 would not have completed otherwise. If the second queue 80 is full, the interaction controller 34 unleashes the particles from the second queue 80 and the third queue 82. These particles then begin to stream through all the PPIMS 54 in the PPIM array 52. The PPIMS 54 then begin the process of calculating interactions between the loaded particles from the first and third queues 78, 82 and the streaming particles from the second and third queues 80, 82.

In an alternative method for managing flow of particles into the PPIM array 52, the interaction controller 34 does not bother to wait until the first and third queues 78 have filled. Instead, the interaction controller 34 loads particles from the first and third queues 78, 82 into the PPIMS 54 as soon as it can. This saves time since the PPIM array 52 no longer has to wait until all particles have arrived before it begins to load particles.

Once the particles are all loaded into the PPIM array 52, the interaction controller 34 begins streaming particles into the PPIM array 52 from the second queue 80 and the third queue 82. This occurs even though the second queue 80 may not yet have received all particles designated for streaming.

In an alternative practice, it is useful to regard the queues shown in FIG. 7 as logical queues that are assembled by selectively choosing queues from a subset of the set of all physical queues. The particles that are placed in these logical queues are obtained by selecting a subset of the set of physical queues. The choice of which subset to select depends on the neighbors of whatever sub-box in question. This allows the flexibility to re-use physical queues on an as-needed basis.

In the course of being streamed through the PPIMS 54, each streaming particle from the second and third queues 80, 82 encounters each stored particle from the first and third queues 78, 82. At each such encounter, a determination must be made concerning whether or not an interaction should be computed. If the answer is "yes," the force that results from interaction between the stored particle and the streaming particle is calculated. These forces are accumulated as they are calculated. Once the streaming particle has traversed the PPIM array 52, the total force acting on the particle is sent to an output 56.

A test must therefore be devised to answer the question, "Should an interaction between these two particles be computed?"

One test for deciding whether or not an interaction should be computed is to ask whether or not the distance between particles is close enough to make computation worthwhile. If two particles are too far apart, no interaction will be calculated.

However, although this test is a good approximation, it is complicated by the fact that sometimes interactions between particles should not be calculated even if the particles are close together. This complication arises in molecular dynamics because atoms can be covalently bonded together to form molecules. In that case, the forces that hold these particles in a bond easily dwarf the inter-particle forces that are being simulated. In known simulation machines, these interactions are still calculated, but are later removed in a correction pipeline.

To remedy this deficiency, and to thereby eliminate the need for a correction pipeline, each particle is associated with a topological identifier that communicates the nature of a topological relationship between that particle and other nearby particles. Without loss of generality, this topological identifier will be discussed in connection with atoms that bond together with other atoms to form molecules, and in particular, biological macromolecules such as proteins and lipids.

Figure 4:
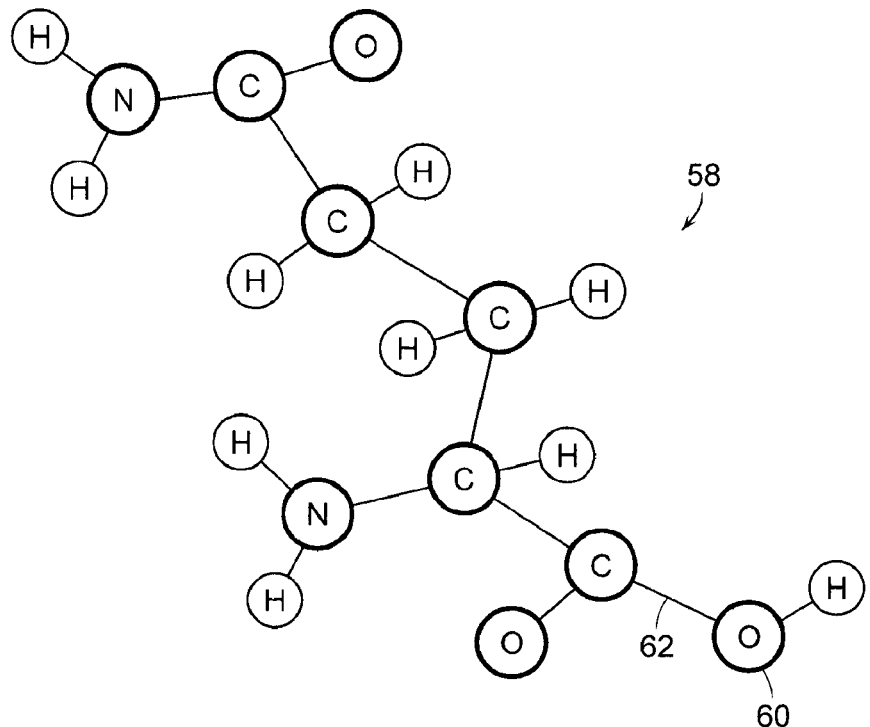
FIG. 4 shows a structural formula for a molecule.

Referring to FIG. 4, a molecule 58 can be represented as a graph in which nodes represent atoms 60 and edges represent bonds 62 between atoms 60. The number of edges separating the two atoms 60 in the molecule 58 can be used to define a topological distance between atoms 60. This topological distance can then be used as a basis for suppressing the computation of an interaction between two atoms. The result will be that for two atoms that are next to each other in a molecule, no interaction will be computed. But if two atoms are on opposite ends of a macromolecule, an interaction may be computed.

Figure 5:
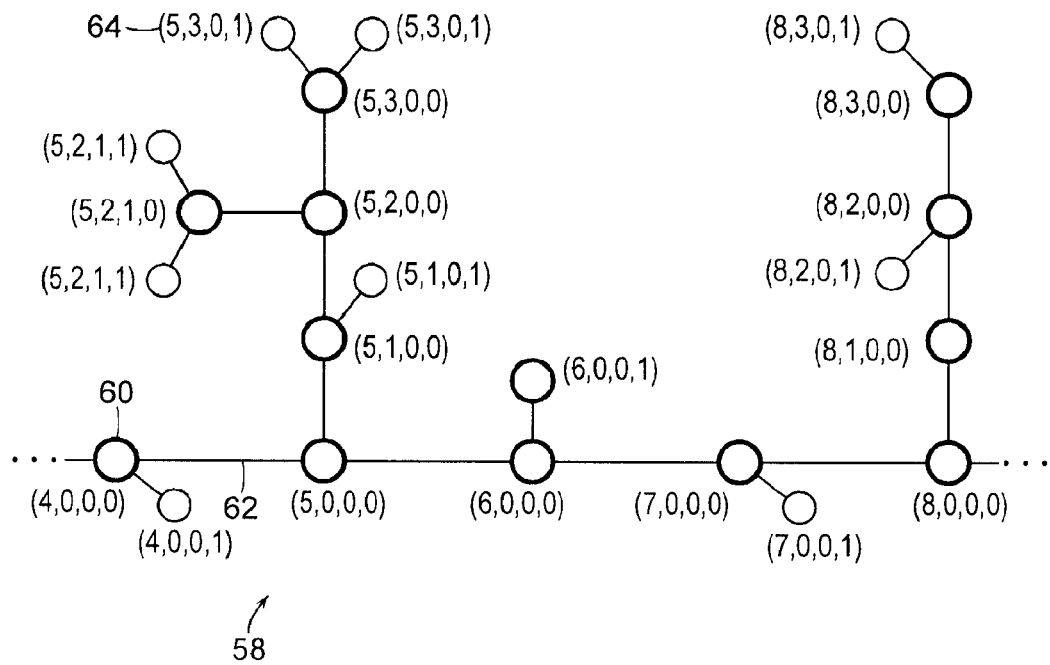
FIG. 5 shows topological identifiers for a molecule.

Referring now to FIG. 5, the topological identifier 64 is a short descriptor that is unique to an atom 60. This uniqueness extends across different molecules.

The topological identifier 64 encodes topological relationships between atoms 60 in a molecule 58. Thus, by comparing the topological identifiers 64 of two atoms 60, it is possible to define a topological distance between the two atoms 60. This enables determination, with high accuracy, of whether an interaction between those atoms 60 should be excluded even if those atoms are otherwise close enough so that interaction would normally be calculated.

Comparing topological identifiers 64 therefore avoids the vast majority of corrections that would normally have been carried out in a correction pipeline, and also avoids wasteful computation. As will be discussed below, there are some special cases where computations will be carried out even if they should not be. However, there are so few of these cases that correction of the calculation can be done by software instead of by having a separate hardware correction pipeline.

The implementation of topological identifiers 64 described herein relies on the fact that many molecules 58 feature a backbone of atoms with primary side-chains branching off the backbone. These primary side-chains can have secondary side-chains. These secondary side-chains can have tertiary side-chains and so an ad infinitum. However, it has been found that most molecules 58 of interest have a backbone with primary side-chains branching off the backbone, and secondary side-chains branching off the primary side-chains. Thus, a practical implementation requires that only primary and secondary side-chains be accounted for.

In the embodiment described herein, each atom 60 is assigned an integer quartet. The members of the quartet identify a backbone, primary and secondary side-chains, and a termination flag. More generally, the topological identifier is an integer tuple with N+2 elements, where N is the number of levels of side chains to be accounted for. In the present embodiment, N=2 because only a primary and secondary side-chain are to be accounted for.

For any atom 60, the first element of the quartet is a backbone identifier that identifies that atom's associated backbone atom. Where an atom 60 is itself the backbone atom, for purposes of assigning the first element, that atom 60 is considered to be associated with itself. All atoms of side-chains that ultimately connect to the same backbone atom would have the same backbone identifier.

The second element of the quartet is a primary side-chain identifier that identifies the primary side-chain associated with the atom 60. The primary side-chain has an atom 60 that is bonded directly to the backbone. All atoms that are in the same side-chain, or are in side-chains connected to that same side-chain would have the same primary side-chain identifier.

The third element of the quartet is a secondary side-chain identifier that defines the second level side-chain associated with the atom.

Finally, the fourth element is a terminal flag that identifies whether or not the atom is a terminal atom. A terminal atom is one that is bound to the rest of the molecule by only one covalent bond. As used herein, the term "covalent bond" is independent of the number of electronic orbitals participating in the bond, and therefore includes double bonds and triple bonds.

It should be apparent that the above scheme is recursive in nature and can be extended to any number of side-chains by simply adding suitable elements between the terminal flag and the backbone identifier.

In the illustrated embodiment, the topological identifier is an integer quartet (n, m, k, t). Backbone atoms are identified as (n, 0, 0, 0). Atoms in a primary side-chain off the nth backbone atom are identified as (n, m, 0, 0) where m is an integer greater than or equal to 1 that represents the distance along the chain between that atom and the backbone atom. Atoms in a secondary side-chain are identified as (n, m, k, 0) where k is an integer greater than or equal to 1 that represents the distance between that atom and the atom at which the secondary side-chain intersects the primary side-chain, (n, m, 0, 0). A terminal atom, which only has a single neighbor, has its terminal flag set to 1. Thus, a terminal atom that has, as its neighbor, atom (n, m, k, 0) will have as its topological identifier 64 the integer quartet (n, m, k, 1).

FIG. 5 shows a graph corresponding to portion of a macromolecule with atoms having the relevant topological identifiers as assigned by the foregoing rules. The illustrated graph shows five backbone atoms numbered 4 through 8. Consistent with the foregoing rules, these are numbered (n, 0, 0, 0) for n=4 to 8.

The atom attached to backbone atom 4 is a terminal atom because it has only one neighbor. Consistent with the rules, its quartet is the same as its neighbor's quartet, i.e. backbone atom 8's quartet, except its terminal flag is set to 1. Terminal atoms can also be found attached to backbone atoms 6 and 7 with corresponding quartets built according to the same rule.

The assignment of topological identifiers to side-chains can be seen by inspecting the identifiers of atoms that are in the side-chain off of backbone atom 5. As shown, each quartet for all atoms that ultimately connect to backbone atom 5 will have n=5. All atoms in the same primary side-chain have the same value of m, while all atoms in the same secondary side-chain have the same value of k.

The topological distance between two atoms having integer quartets $(n_1, m_1, k_1, t_1)$ and $(n_2, m_2, k_2, t_2)$ resolves into three cases.

In the first case, the atoms are attached to different backbone atoms and therefore have different backbone identifiers. This means that $n_1 \neq n_2$. In such a case, the distance is obtained by taking the magnitude of the difference between the backbone identifiers and adding it to the sum of all the remaining elements of the two integer quartets:

$$|n_1-n_2|+m_1+m_2+k_1+k_2+t_1+t_2$$

In the second case, the two backbone identifiers are the same, but the two atoms are on different primary side-chains. Thus, $n_1=n_2$ but $m_1 \neq m_2$. In that case, the distance is identical to that for the first case, but instead of adding together the primary side-chain identifiers, one evaluates the magnitude of their difference:

$$|n_1-n_2|+|m_1-m_2|+k_1+k_2+t_1+t_2$$

In the third case, the two atoms are on the said primary side-chain but they are on different secondary side-chains. This means that $n_1=n_2$ and $m_1=m_2$, but $k_1 \neq k_2$. In that case, the distance is computed the same way as the second case, but instead of adding together the secondary side-chain identifiers, one evaluates the magnitude of their difference:

$$|n_1-n_2|+|m_1-m_2|+|k_1-k_2|+t_1+t_2$$

The foregoing method for assigning a topological identifier 64 assumes that the graph of a molecule 58 is an acyclic graph with at most one side-chain emanating from any atom. While this is true for most molecules of interest, there are exceptions. In such cases, a small number of edges are removed from the molecules graph until this condition is met.

Figure 6:
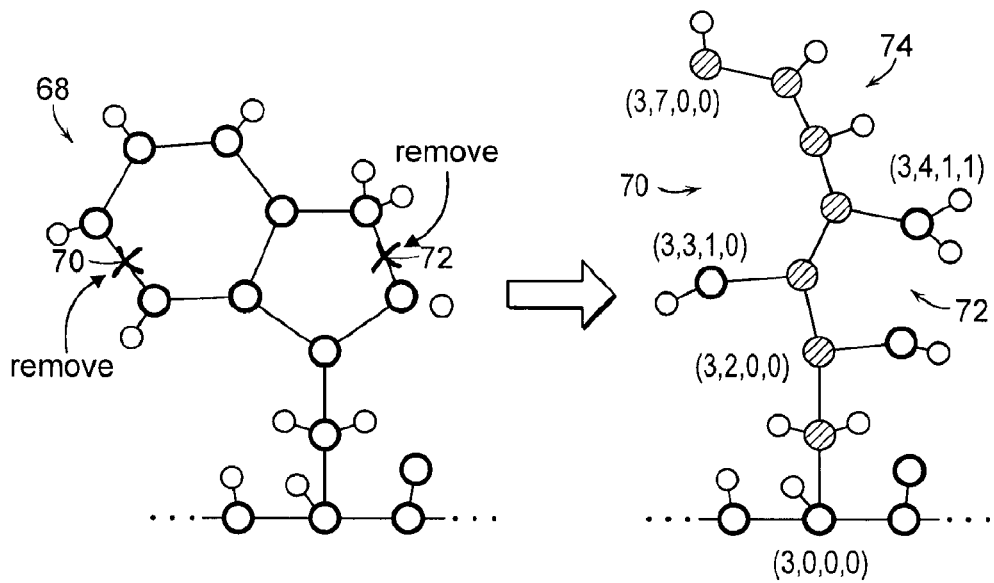
FIG. 6 shows how a cyclic graph for a molecule is modified to accommodate tagging of its atoms by topological identifiers.

FIG. 6 shows an example of a molecule 68 having a cyclic graph. The aforementioned method for assigning topological identifiers does not work when the molecule's graph is cyclic or contains cyclic portions. To accommodate this case, it is necessary to remove two edges 70, 72 from the graph to open up the cyclic portions, thus yielding a corresponding acyclic molecule 74. A correction is later carried out in software to address this irregularity.

An atom's topological identifiers and its position location are bundled with its position as it makes its way through the PPIM array 52. As a result, the encoding must be as compact as possible.

As a practical matter, in molecules of interest, most side-chains are short. For most lipids and proteins, three bits is sufficient to encode the primary side-chain identifier, and one bit is enough to encode the secondary side-chain identifier. One more bit is needed to encode the terminal flag. Thus, the remaining bits can be used to encode the backbone identifier.

In some cases, a chemical system is too large for all backbone identifiers to be encoded because there are not enough bits allocated to carry out the encoding. In other cases, side-chains cannot be encoded in the bits available. Both of these cases, like the case in which the molecule has rings, must also be corrected in software.

During the course of evaluating quantities, such as interparticle forces, it is often necessary to carry out computations that involve evaluating a function of an argument. Evaluating a function, particularly a transcendental function, is a time-consuming task. To speed up this task, it is known to simply look up the value of the function for a particular argument in a look-up table. However, a table that provides low approximation error would be prohibitively large. Another approach is to divide the domain of the function into parts and to approximate the desired function using a parametric form, such as a cubic form. In such cases, a table provides a mapping from a domain region to coefficients of a cubic polynomial. A non-uniform partition of the domain can be used to provide a finer partition in those parts of the domain in which the cubic polynomial does not match the function well, for example, in those parts of the domain in which the function to be approximated is changing fast. Conversely, coarser partitions can be used where the match is good.

In some cases, the function's value changes so rapidly for certain regions of its domain that even using the cubic polynomial would require that the look-up table of cubic coefficients have prohibitively many entries in order to adequately model the function in those portions of its domain.

Figure 8:
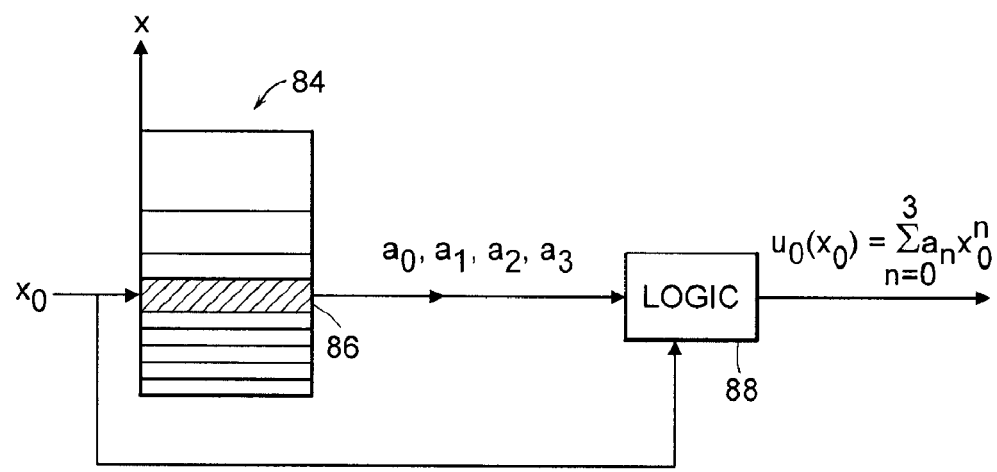
FIG. 8 shows a table for use in piecewise approximation of a function.

FIG. 8 illustrates a look-up table 84 for a function that is piecewise approximated by a cubic polynomial. To obtain the value of the function $u(x_o)$ for a particular value of $x_o$, one looks up the entry 86 corresponding to that portion of the domain that includes $x_o$. This entry 86 yields the coefficients of the cubic polynomial, which can then be evaluated using suitable combinatorial logic 88 to yield a value of the function $u(x_o)$.

Naturally, since the approximation is a piecewise one, the coefficients of the polynomial change throughout the approximated function's domain. In fact, this is precisely why there have to be multiple entries in the table 84. As is apparent from FIG. 8, for certain regions of its domain, the approximated function changes so rapidly that the entries in the table are only valid for very small such regions. Of course, one can easily solve this problem by having more table entries, each of which covers a smaller part of the function's domain. But it is desirable to avoid this because such tables consume large amounts of die-space.

Figure 9:
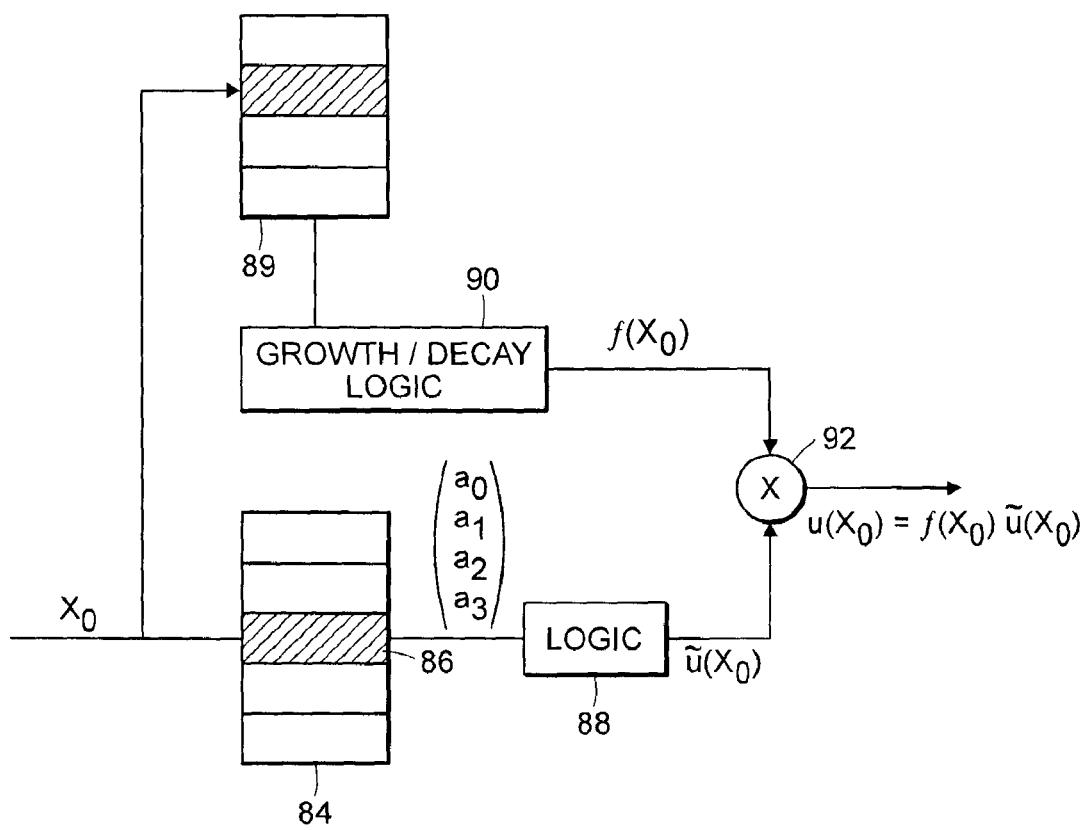
FIG. 9 shows a smaller table with accompanying logic to carry out substantially the same piecewise approximation as the table of FIG. 8.

In an alternative embodiment, shown in FIG. 9, the table 84 has fewer entries, even for those parts of the approximated function's domain in which the approximated function changes rapidly. To obtain an approximated value of the function $u(x_o)$ for a particular value of $x_o$, one looks up the entry 86 corresponding to that portion of the domain that includes $x_o$. This entry 86 yields the coefficients of a cubic polynomial. These coefficients can then be used by suitable combinatorial logic 88 to yield a first approximation of the value of the function at the argument $x_o$, namely $\tilde{u}(x_o)$. To improve this first approximation, the argument $x_o$ is also provided to a look-up table 89 that outputs one or more parameters based on the argument. The one or more parameters are then provided to growth/decay logic 90. The growth/decay logic 90 implements functions that are easily executed in logic and that can yield a second approximation. The output of the growth/delay logic 90 is a value of a function $f(x_o)$. This value and the first approximation $\tilde{u}(x_o)$ are provided to a multiplier 92, the output of which is the second approximation $u(x_o) = \tilde{u}(x_o) \, f(x_o)$. In a preferred embodiment, $f(x_o)$ is $x_o^k \cdot \exp(-x_o^m)$, where k and m are the parameters obtained from the look-up table 89 for a particular value of $x_o$.

It is known to use the PPIM array 52 in connection with charge spreading and force interpolation using GSE methods described in Shan et al., "GRID BASED COMPUTATION FOR MULTIPLE BODY SIMULATION," U.S. Pat. No. 7,526,415, issued Apr. 28, 2009, the contents of which are herein incorporated by reference. The mathematical basis for the methods applied in Shan are set forth in Shan, et al., "GAUSSIAN SPLIT EWALD: A FAST EWALD MESH METHOD FOR MOLECULAR SIMULATION, J. Chem. Phy. 122 054101 (2005), the contents of which are herein incorporated by reference. Details on how particles and grid locations are distributed in the PPIM array 52 are described in Shaw et al., "PARALLEL COMPUTER ARCHITECTURE FOR COMPUTATION OF PARTICLE INTERACTIONS," U.S. Patent Publ. 2013/0091341, published Apr. 11, 2013, the contents of which are herein incorporated by reference.

In an improvement of the method described therein, in which all grid locations are passed into the PPIM array 52, an alternative method exploits the fact that grid locations are not randomly located but actually have some spatial regularity. By exploiting this regularity, it becomes possible to pass selected locations into the array and derive the grid locations from those selected locations.

For example, let X be a set of m grid locations $(x_1, x_2 \ldots x_m)$ where each $x_i$ is a position vector having a dimensionality that is appropriate to the simulation space. According to the prior art method, to pass the points grid locations into X, one would pass all m points into the PPIM array 52.

In an improved method, there exists a set Y of n locations $(y_1, y_2 \ldots y_n)$ where n<m. There also exists a rule R such that X=R(Y). Thus, rather than pass X into the PPIM array 52 one only as to pass Y and implement the rule R in the PPIM array 52 to reconstruct X. This amounts to a compression technique, with the extent of compression being dependent on the ratio of m to n.

For example, if two vectors in the set X were $(x, y, z_1)$ and $(x, y, z_2)$, then one could simply pass a set Y that included the vector $(x, y, (z_1+z_2)/2)$. Then, if one knew the grid spacing, one could derive the original two vectors from the set X. Alternatively, the set Y could just equal every other point from set X, in which case one could reconstruct the original set X by adding the appropriate grid spacing to the appropriate coordinates in the vectors in Y.

In one method, the set Y of locations is loaded into the PPIM array 52 and atoms are streamed through the PPIM array 52. This procedure is used to carry out charge spreading. In another practice, the roles are reversed, and atoms are loaded into the PPIM array 52 while the set Y of locations is streamed through the PPIM array 52. This procedure is used to carry out force interpolation.

In one embodiment of the simulation machine 10, the particles that arrive at the interaction tile 16 for processing are always associated with a current time step. However, an alternative embodiment introduces a phase bit associated with data packets carrying particle data into the interaction tile 16. The phase bit's value is associated with a particular time step. This provides a way to distinguish between particles in two different time steps. As a result, it is possible for the interaction tile 16 to receive data packets associated with two time steps.

In an embodiment that accommodates a phase bit, the interaction controller 34 maintains queues 36 associated with each value of phase bit. Upon receiving a particle, the phase bit of the particle is inspected and the particle is placed in a queue that is appropriate to the phase bit. The phase bit thus permits the interaction tile 16 to receive data associated with different time steps, and thereby eliminates the need to synchronize the interaction tiles 16 and the flex tiles 14. In operation, only queues corresponding to the current time step are loaded into the PPIM 54.

Having described the invention and a preferred embodiment thereof, what is claimed as new, and secured by letters patent is:

The invention claimed is:

1. A method comprising causing a computer to determine that a topological distance between two particles is less than a threshold, wherein said computer is a simulation machine for molecular dynamic simulation that has been provided with said threshold, said simulation machine comprising a plurality of nodes connected to each other by a network, said nodes collectively representing a volume with each node corresponding to a particular portion of said simulation space, wherein a topological relationship between said nodes in said network corresponds to spatial relationship thereof in said simulation space, wherein said simulation volume is occupied by particles that interact with each other and that are part of a macromolecule, wherein said topological distance between said particles, which is to be compared with said threshold, depends on a number of edges that separate said particles from each other in said macromolecule, wherein said two particles whose topological distance from each other is to be compared with said threshold are among said particles, wherein said simulation volume comprises node boxes, each of which is handled by one of said nodes, wherein each of said nodes is implemented as an application specific integrated circuit that comprises a combination of first hardware elements that are especially designed to perform pairwise interactions and second hardware elements whose function is to provide potentially interacting particles to said first hardware elements, wherein said potentially interacting particles include particles separated by a topological distance that is less than said threshold.

2. The method of claim 1, further comprising, based on said determination, causing said computer to suppress computation of an interaction between said two particles.

3. The method of claim 1, further comprising providing a computer-readable graph representing a relationship between said particles, wherein said topological distance depends at least in part on a number of edges between said two particles in said graph.

4. The method of claim 1, wherein determining that a topological distance between said two particles is less than a threshold comprises tagging a first of said particles with a first topological identifier indicative of a topological relationship between said first particle and a set of particles of which it is a part.

5. The method of claim 4, wherein said first particle is an atom and said set of particles is a molecule formed by covalent bonds between pairs of particles.

6. The method of claim 4, further comprising tagging a second of said particles with a second topological identifier and determining a topological distance between said first and second particles based on said first and second topological identifiers.

7. The method of claim 6, wherein each of said first and second topological identifiers comprises a backbone identifier.

8. The method of claim 6, wherein each of said topological identifiers comprises at least one primary side-chain identifier.

9. The method of claim 6, wherein each of said topological identifiers comprises a termination flag.

10. The method of claim 6, wherein each of said first and second topological identifiers comprises at least one secondary side-chain identifier.

11. The method of claim 6, further comprising calculating a topological distance based on said first and second topological identifiers, wherein calculating said topological distance comprises adding together a magnitude of a difference between backbone identifiers of said first and second topological identifiers, primary side-chain identifiers of said first and second topological identifiers, secondary side-chain identifiers of said first and second topological identifiers, and terminal identifiers of said first and second topological identifiers.

12. The method of claim 6, further comprising calculating a topological distance based on said first and second topological identifiers, wherein calculating said topological distance comprises adding together a magnitude of a difference between primary side-chain identifiers of said first and second topological identifiers, secondary side-chain identifiers of said first and second topological identifiers, and terminal identifiers of said first and second topological identifiers.

13. The method of claim 6, further comprising calculating a topological distance based on said first and second topological identifiers, wherein calculating said topological distance comprises adding together a magnitude of a difference between secondary side-chain identifiers of said first and second topological identifiers, and terminal identifiers of said first and second topological identifiers.

14. The method of claim 3, further comprising determining that said graph has a cyclic portion and modifying said graph to eliminate said cyclic portion prior to assigning topological identifiers to particles represented in said graph.

15. A non-transitory and tangible computer-readable medium having encoded thereon software that, when executed by a computer system, causes execution the method of claim 1.

16. An apparatus comprising a computer system configured to execute the method of claim 1.

17. An apparatus comprising a molecular dynamics simulator configured to execute the method of claim 1.

18. The method of claim 1, further comprising, based at least in part on said determination, avoiding a correction that would otherwise be carried out in a correction pipeline.

19. The method of claim 8, wherein each of said first and second topological identifiers comprises a primary side-chain identifier.

20. The method of claim 8, wherein each of said first and second topological identifiers comprises a secondary side-chain identifier.

21. The method of claim 1, further comprising assigning an integer quartet to each of said particles.

22. The method of claim 21, wherein said integer quartet comprises first, second, third, and fourth members, wherein said first member represents a backbone, wherein said second member represents a primary side chain, wherein said third member represents a secondary side chain, and wherein said fourth member represents a termination flag.

23. The method of claim 1, further comprising assigning a tuple to each of said particles, said tuple comprising a number of members, wherein said number is two more than a number of levels of side chains to be accounted for.

24. The method of claim 22, wherein said second particle is one of a set of particles that defines a molecule formed by covalent bonds between said particles of said set of particles, wherein said termination flag indicates that said first particle is bonded to said set of particles by at most one bond.

25. The method of claim 1, further comprising determining that said particles are on different backbones of a macromolecule.

26. The method of claim 1, further comprising determining that said particles are on different side chains of a macromolecule.

27. The method of claim 1, further comprising determining that said particles are on the same primary side chain of a macromolecule and on different secondary side chains of said macromolecule.

28. The method of claim 1, wherein said application specific integrated circuit comprises flex tiles, interaction tiles, a host interface, and a logic analyzer, wherein said host interface provides communication with an external host via a PCI link, wherein said logic analyzer is configured to capture and store node activity, wherein each of said nodes comprises communication interfaces and an on-chip mesh network, wherein said communication interfaces enable data transmission between neighboring nodes in each of three local coordinate directions, and wherein said on-chip mesh network provides data transmission between components of said node.

29. The method of claim 28, wherein each flex tile comprises geometry cores, a network interface, a common memory, and a dispatch unit, wherein each geometry core has an associated memory, wherein each flex tile comprises a network interface for communication with other components of said node, wherein said dispatch unit provides hardware support for fine-grained event-driven computation, and wherein said common memory is available to said geometry cores.

* * * * *